(12) United States Patent
Costa

(10) Patent No.: US 8,722,066 B2
(45) Date of Patent: May 13, 2014

(54) DEVICES AND METHODS FOR WEIGHT CONTROL AND WEIGHT LOSS

(75) Inventor: Paolo Costa, Tiburon, CA (US)

(73) Assignee: Primigenia, LLC, Wilmington, DE (US)

( * ) Notice: Subject to any disclaimer, the term of this patent is extended or adjusted under 35 U.S.C. 154(b) by 0 days.

(21) Appl. No.: 13/431,076

(22) Filed: Mar. 27, 2012

(65) Prior Publication Data

US 2012/0251589 A1 Oct. 4, 2012

Related U.S. Application Data

(60) Provisional application No. 61/468,802, filed on Mar. 29, 2011.

(51) Int. Cl.
| | |
|---|---|
| *A61K 9/00* | (2006.01) |
| *A61K 9/48* | (2006.01) |
| *A61K 47/00* | (2006.01) |
| *A61K 47/36* | (2006.01) |
| *A61K 47/38* | (2006.01) |
| *A61K 31/736* | (2006.01) |

(52) U.S. Cl.
USPC ........... 424/400; 424/439; 424/451; 424/484; 424/485; 424/486; 424/488

(58) Field of Classification Search
CPC ... A61K 45/06; A61K 38/1709; A61K 31/41; A61F 2/2412; A61F 28/5044; A23L 1/053; A23L 1/293; A23L 1/308; A23L 2/52
See application file for complete search history.

(56) References Cited

U.S. PATENT DOCUMENTS

| 6,677,318 B1 * | 1/2004 | Beisel ........................... 514/54 |
| 2007/0207186 A1 * | 9/2007 | Scanlon et al. ............... 424/424 |

FOREIGN PATENT DOCUMENTS

WO  WO 2005074378 A2 *  8/2005

OTHER PUBLICATIONS

Lee et al., "Review: Biomedical applications of collagen", International Journal of Pharmaceutics 221 (2001) pp. 1-22.*
Bhattarai et al., "Chitosan-based hydrogels for controlled, localized drug delivery", Advanced Drug Delivery Reviews 62 (2010) pp. 83-99.*
MedlinePlus, "Nitrofurantoin", Feb. 22, 2010, pp. 1-3, <http://www.nlm.nih.gov/medlineplus/druginfo/meds/a682291.html>.*

* cited by examiner

*Primary Examiner* — Tracy Vivlemore
*Assistant Examiner* — Monica Shin
(74) *Attorney, Agent, or Firm* — Lewis Roca Rothgerber LLP

(57) ABSTRACT

The present invention provides, compositions, devices, and methods for affecting, among other things, weight loss and/or weight control, by sequestering nutrients or other compounds such as toxins from absorption in the digestive tract. The compositions, devices, and methods employ one or more members made of a compressible, absorbent matrix material. In various embodiments, the matrix material is suitable for routine use. The compressible absorbent matrix material has a size, shape and/or geometry configured for efficient packing into a small space, and/or configured to absorb and substantially retain digested material in the stomach. The devices and compositions may further comprise one or more hydrogel(s), soluble or insoluble fibers, waxes and/or gums to provide the desired mechanical properties and/or absorptive or shielding properties.

20 Claims, 13 Drawing Sheets

DEVICES AND METHODS FOR WEIGHT CONTROL AND WEIGHT LOSS

CROSS SECTION TO RELATED APPLICATIONS

The present application claims the priority benefit of U.S. provisional application No. 61/468,802, filed Mar. 29, 2011, and entitled DEVICES AND METHODS FOR WEIGHT CONTROL AND WEIGHT LOSS, the entire disclosure of which is hereby incorporated by reference.

This application is related to U.S. Provisional Application No. 61/443,123, filed Feb. 15, 2011, which is hereby incorporated by reference.

FIELD OF THE INVENTION

The present invention relates to devices, compositions, and methods for, among other uses, reducing the amount of nutrients or other compounds absorbed in the GI tract from ingested food.

BACKGROUND OF THE INVENTION

The term "overweight" refers to body weight above a normal range. Overweight and obesity are determined by calculating the body mass index (BMI), the weight in kilograms divided by height in meters squared. Overweight is generally defined as a BMI of 25 to 29.9 kg/m$^2$, obesity is generally defined as a BMI of ≥30 kg/m$^2$, and severe obesity is generally defined as a BMI≥40 kg/m$^2$ (or BMI≥35 kg/m$^2$ in the presence of other medical comorbidities). A BMI less than about 22.0 kg/m$^2$ is ideal, though this may be a difficult and perhaps unrealistic goal for many individuals.

Overweight and obesity are worldwide health epidemics, with increasing prevalence. In the United States, more than two-thirds of Americans are overweight and 26-55% are obese based on data collected in 2007 by the Centers for Disease Control and National Institutes of Health. Globally, overweight and obesity affects both established and developing countries. For example, about 23% of the population in the United Kingdom is obese, compared to about 11-23% in Mexico, approximately 30-40% in South Africa, and about 10% in Pakistan.

Overweight and obesity are associated with Many health risks including type 2 diabetes mellitus, hypertension, dyslipidemia, coronary heart disease, cancer and stroke among others, as well as premature death. Compared to normal weight individuals, a BMI of 26.5 to 29.9 kg/m$^2$ is associated with a 1.5 times increased risk of death. Those with a BMI≥30 kg/m$^2$ have a 2-3 fold increased risk of all-cause mortality. The economic implications are great; a Brookings institute publication quoted the cost to the United States of overweight and obesity to be at least $147 billion annually. The rationale for weight reduction is clear, from both a medical and economic perspective.

Currently available methods to decrease weight include behavior modification (dietary change and exercise regimens), drug therapy, and bariatric surgery. Drug therapy is indicated in patients who have failed to achieve weight loss goals through diet and exercise alone. The FDA has approved two classes of medications explicitly for use in weight loss. Sympathomimetic drugs (e.g., phendimetrazine, diethylpropion, phentermine) stimulate the release of norepinephrine and/or inhibit its reuptake into nerve terminals. In lay terms, this effect is analogous though much stronger than that produced by caffeine. Sympathomimetics cause appetite suppression but also may cause hypertension and potentially myocardial infarction, and as a result are limited to <12 weeks of use by the FDA. Ephedrine is a member of this class that was recently removed from the market because of these adverse side effects.

Malabsorptive drugs are the other medication class that is FDA approved for use in obesity. Orlistat is the only representative of this group. Orlistat alters fat digestion by inhibiting pancreatic lipase, resulting in the malabsorption of 30% of ingested fat. Instead of being taken up by the body, this fat is excreted in stool. Orlistat is the only FDA approved medication for obesity that is acceptable for long term use (up to 4 years).

For patients with severe obesity, the only proven mechanism of long-term weight loss is bariatric surgery. Bariatric surgery effects weight loss through either malabsorption and/or restriction. Malabsorption (as with Orlistat above) means the incomplete absorption of ingested food. The body does not absorb the full amount of calories present in a meal or in a given food item. Restriction means a reduction in the size of the stomach, with resultant early satiety and reduced food consumption.

Overweight and obese patients who do not meet BMI criteria for severe obesity do not have surgery as an available option for weight loss, as insurance coverage for these procedures is typically limited to the severely obese. Accordingly, overweight and obese patients have access to only one FDA approved medication for weight loss. Thus, there exists a great need for weight loss and weight control alternatives.

SUMMARY OF THE INVENTION

The present invention provides, compositions, devices, and methods for affecting (among other things) weight loss and/or weight control, by sequestering nutrients or other compounds (e.g., alcohol or toxins) from absorption in the digestive tract. In various embodiments, the compositions, devices, and methods, which employ a compressible, absorbent matrix material, are suitable for routine use.

In one aspect, the present invention provides a device or composition comprising one or more members of a compressible absorbent matrix material designed to absorb and substantially retain nutrient material in the digestive tract, such as nutrient material present in the stomach after a meal. The device or composition may further employ one or more hydrogel(s), soluble or insoluble fibers, waxes and/or gums to provide the desired mechanical properties and/or absorptive or shielding properties, as described in detail herein. In some embodiments, the device is in the form of a capsule comprising the matrix material members, which may be in the form of tubes. Alternatively, the device or composition may be a food additive.

In another aspect, the present invention provides a method for absorbing and retaining (e.g., shielding) nutrients or other compounds from the absorptive action of the digestive tract. The method comprises providing the device or capsule for ingestion before, during, or after eating. The subject may be an overweight or obese subject, and the composition or device may be used routinely to affect weight loss. Alternatively, the subject may be of normal weight, but in need of weight control, for example, due to a pattern or history of being overweight.

The orally ingested device or composition in various embodiments contains one or a plurality of "sponges" or "sponge tubes" in a compressed or dense state, and which expand once in the GI tract. The sponge matrix or scaffolding greatly amplifies the volume displaced in the expansion of the sponges. For example, in certain embodiments, the sponge material may itself absorb ten times or more its weight in fluid, which helps to shape the material as in a scaffolding. When the sponge expands it doesn't just absorb ten times its volume, but soaks in all the fluids contained in the void spaces of the scaffolding. That is, the "chambers" or "holes" of the sponge dramatically magnify the volume of fluids absorbed. These fluids will be then trapped inside the scaffolding of the sponge by hydrogels in the sponge cell walls that seal each chamber.

More particularly, the sponge absorbs portions of chyme suspension in the stomach, reducing the amount of food available for absorption in the small intestine. In this manner, calories are "sequestered" from the body, promoting weight loss. The device or composition design maximizes the capacity and/or efficiency for nutrient absorption (and concomitant sequestration of the nutrients) and avoids the side effects associated with drug-based treatments for obesity. For example, the material and/or geometry of the matrix material, together with one or more hydrogel(s), soluble and/or insoluble fiber(s), waxes) and gum(s) provides the desired mechanical properties, including efficient packing and desired elasticity and/or expansion of the matrix material, as well as the desired properties for absorption of nutrients and subsequent sequestering and shielding from digestive action.

In various embodiments, the present invention helps to reverse a trend in the food industry, which has progressively reduced fiber from foodstuffs and has replaced it with sugars. The present invention thus also supplies fiber to the diet while eliminating absorption of sugars.

In various embodiments, the present invention absorbs fluids rich in sugars and/or alcohol, which are typically soluble, and consequently, more absorbable by the GI than other less soluble nutrients. Further, sugars and/or alcohol may not be beneficial for health. Such fluids may then be sequestered by the compositions and devices in their native state and/or in a gelled or a mucilaginous state. For example, the fluids may be sequestered by absorption, reaction, or association with other compounds like soluble fibers. Accordingly, the body will "see" (e.g., will be able to absorb during digestion) fewer nutrients (e.g., sugars, carbohydrates, fats, alcohol and spirits, etc.), and on the contrary, will "see" more beneficial fibers.

In various embodiments, the present invention provides sequestration in the stomach or in the gastrointestinal tract of compounds, liquids (e.g., alcohol), drugs, or other dangerous or toxic substances that were willingly or unwillingly ingested. The composition or device has the potential to absorb and soak ingested material, and gel it and safely and naturally remove it from the body.

In various embodiments, the present invention provides the sequestration of nutrients without changing an individual's usual diet, the usual taste, and the usual quantities of food ingested by the average consumer in a significant fashion.

The device and compositions of the invention may be used routinely or chronically by the overweight and obese for sustained weight loss, or by the normal weight individual for weight control. For example, the device may be used from once to twenty times weekly, for one or several years (e.g., 1, 2, 3, or more years). The device may be used from one to three times daily (e.g., with each meal) for one, two, or three years, or more. Alternatively, it may be used in the short term by normal weight individuals who have eaten excessively, and may wish to decrease the caloric "damage" of their indulgence. Accordingly, the present device and methods may provide a inexpensive, safe solution to obesity and overweight for hundreds of millions people worldwide, with the corresponding benefits in the associated medical comorbidities, life span, health care expenditures and global economic burden.

The device and compositions may be used to absorb and prevent digestion or biological effects of toxins or alcohol that is willingly or unwillingly ingested. In these embodiments, the device or composition need not be used routinely, but may be taken with food that is at risk of containing toxin, or upon knowledge of toxin ingestion, or may be used to avoid or counter the effects of alcohol overconsumption.

DETAILED DESCRIPTION

Figure 1:
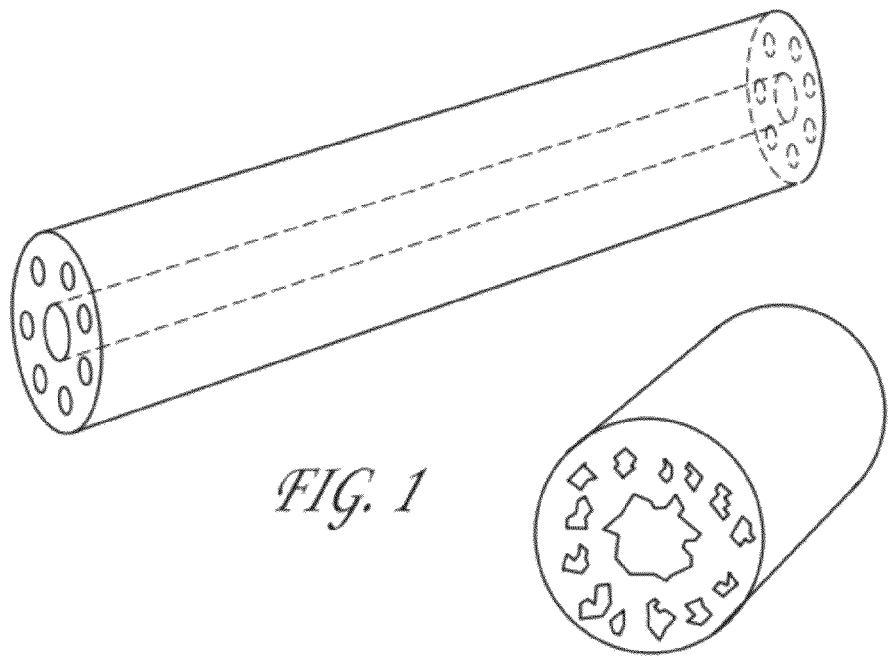
FIGS. 1 to 16 show exemplary designs for the absorbent materials.

The present invention provides, compositions, devices, and methods for affecting, among other things, weight loss and/or weight control, by sequestering nutrients or other compounds such as toxins from absorption in the digestive tract. The compositions, devices, and methods employ one or more members made of a compressible, absorbent matrix material. In various embodiments, the matrix material is suitable for routine use. The compressible absorbent matrix material has a size, shape and/or geometry configured for efficient packing into a small space, and/or configured to absorb and substantially retain digested material in the stomach. The devices and compositions may further comprise one or more hydrogel(s), soluble or insoluble fibers, waxes and/or gums to provide the desired mechanical properties and/or absorptive or shielding properties.

The compositions and devices reduce the caloric absorption by the body of ingested nutrients. The method of operation of the present devices may be referred to as "malabsorption," whereby nutrients are absorbed by the matrix material (e.g., sponge material) and sequestered in the GI tract. Accordingly, the sequestered-nutrients are not metabolized or absorbed by the intestine, and are excreted with the matrix material. The devices are inert and operate in a passive fashion and do not substantially interfere with body metabolism. In essence, the device "shields" ingested nutrients from the absorption action of the intestinal villi and other digestive activity.

The compressible absorbent matrix material may, in some embodiments, be a sponge material, and may be in the form of "sponge tubes" and/or "sponge drops." While tubes may be the most intuitive and simple shape for the matrix material, the matrix material may or may not be tubular in shape, as other geometries will be suitable and/or advantageous in certain embodiments.

The sponge material may be a naturally occurring material or may be an artificially foamed type sponge comprising a multitude of open space, e.g., open or closed "cells" which may be irregular or regular in shape, and defined by the sponge matrix "cell walls". The sponge material may also be a material having an alternation of empty and closed spaces, regular or irregular, having a defined geometry or amorphous, or a mixture of defined and irregular or amorphous spaces. In some embodiments, the sponge material has geometrically engineered structures able to collapse under mechanical, chemical or thermal action, or a combination thereof, and can subsequently assume an expanded shape. The expanded shape may be the original shape (before compression), or another intended shape. The expanded shape generally occurs in response to removal of the mechanical, chemical or thermal action upon interaction with stomach contents or/and chemical interactions with suitable additives present in the device.

The matrix material, when subject to mechanical compression, thermal and/or chemical treatment (e.g., by chemically modifying the material, crosslinking, compounding or covalent bonding compounding, etc.), can be reduced in size and/or volume to a size and/or volume that is much smaller than the original, uncompressed size and/or expanded volume. The compressible property allows for efficient packing of a plurality of matrix material members into a small space, such as a capsule or other vehicle for delivery. For example, the compressed size or volume may be less than about 50% of the expanded size, or in other embodiments, less than about 40%, less than about 30%, less than about 25%, less than about 20%, less than about 15%, less than about 10%, less than about 5%, less than about 1%, less than about 0.5%, or less than about 0.1% of the expanded size or volume. Generally, after release of an applied mechanical compression or chemical constraint (e.g., by chemical reaction, breaking of crosslinking, etc.) or both, the material can assume its original, larger shape.

The mechanism of expansion of the matrix material may also be elastic return, where the material, although not elastomeric per se, may still be stiff enough (e.g., the molecular creep time is sufficiently long) that the material may still at least partially assume its original shape after a period of compression and/or stress.

The matrix material can be mechanically flattened and stacked, or simply compressed, then encapsulated, e.g., in a conventional pharmaceutical capsule for ingestion. The matrix material is generally made of an elastic and/or resilient material which can be compressed and is capable of absorbing liquid and/or material in the digestive tract. The matrix material generally has an internal porosity like a natural sponge. The cells of the sponge or sponge-like material may be random and/or amorphous (e.g., as in typical commercially available artificial or natural sponges). Alternatively, in some embodiments, the cells of the sponge material may be more regular and/or geometrically ordered, like a honeycomb or other geometric and/or volumetric arrangement.

The geometric structure of the matrix material may also provide a magnifying and/or multiplicative effect on the expansion of the present devices and their digestive fluid absorption and/or retention capacity, relative to amorphous and/or non-geometric devices comprising natural fibers. This magnifying and/or multiplicative effect can be at least 2 times, at least 5 times, at least 10 times, at least 50 times, or at least 100 times, relative to an amorphous device (e.g., a device having an irregular shape). Accordingly, a much smaller quantity, mass, volume, dosage or amount of the present device(s) or compositions is required in these embodiments. For example, in some embodiments, a user need only ingest a small pill or capsule (e.g., conventionally sized pill or capsule). In accord with the multiplicative and/or magnifying effect as described herein, such a small pill or capsule may effectively provide a large capacity for absorption of digestive fluids and, consequently, sequestration or shielding thereof from absorption by the body.

Figure 17:
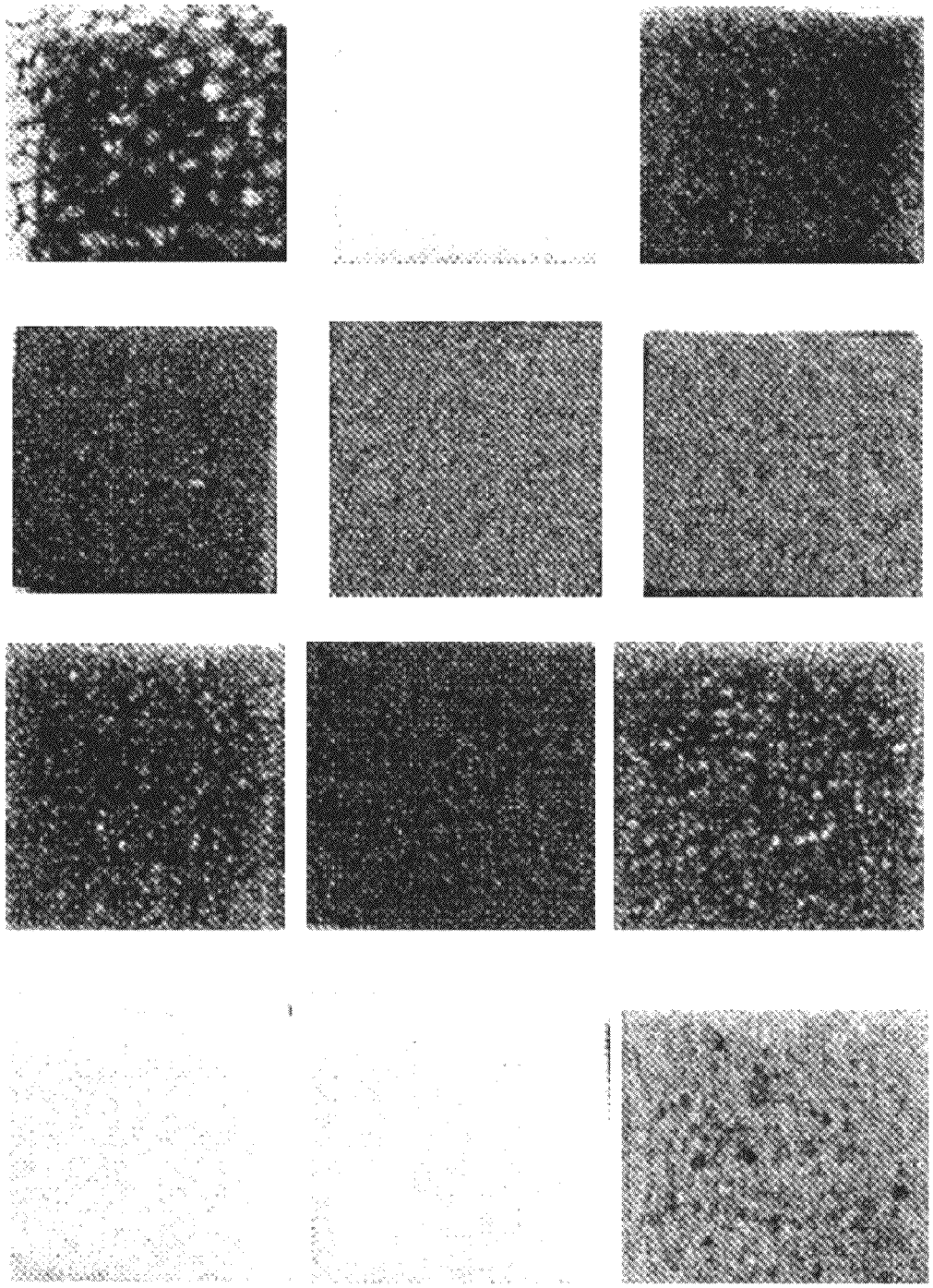
FIGS. 17 to 20 show exemplary absorbent materials.
Figure 18:
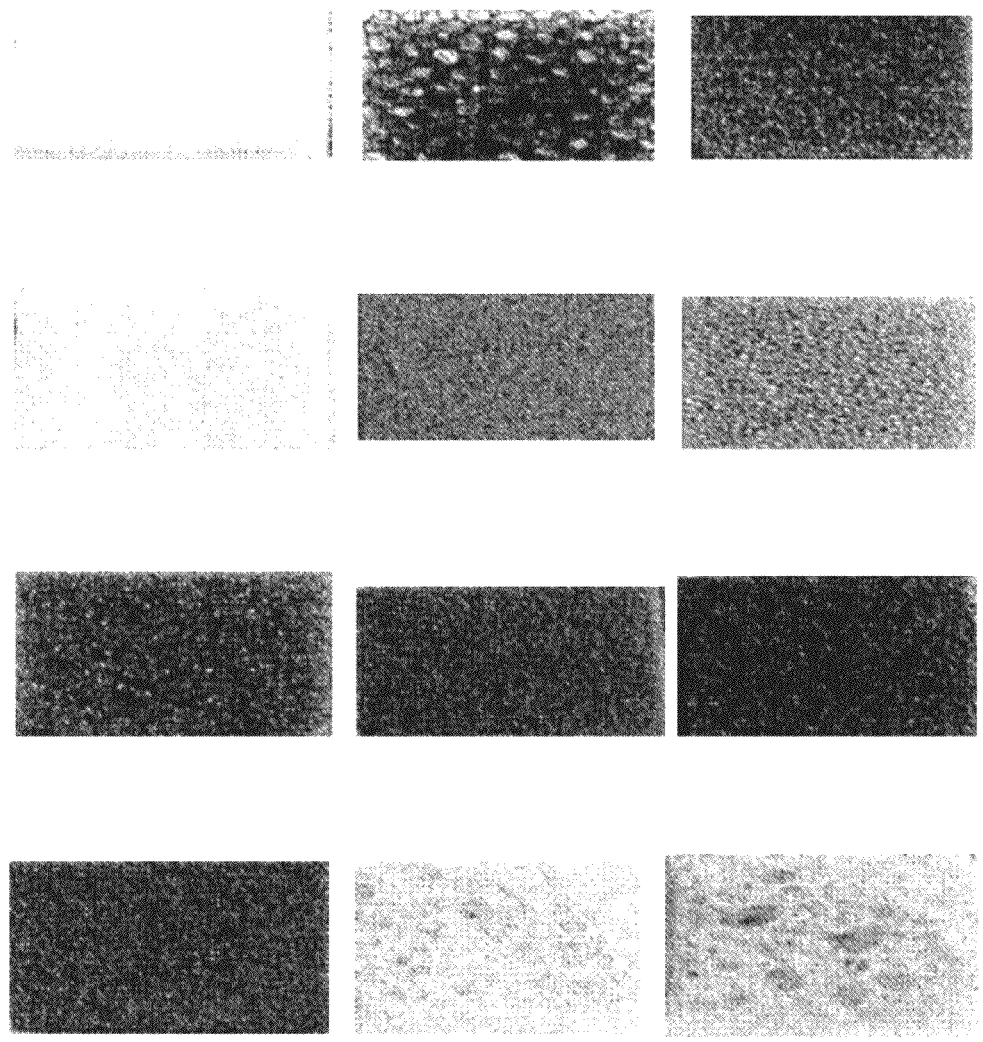
Figure 19:
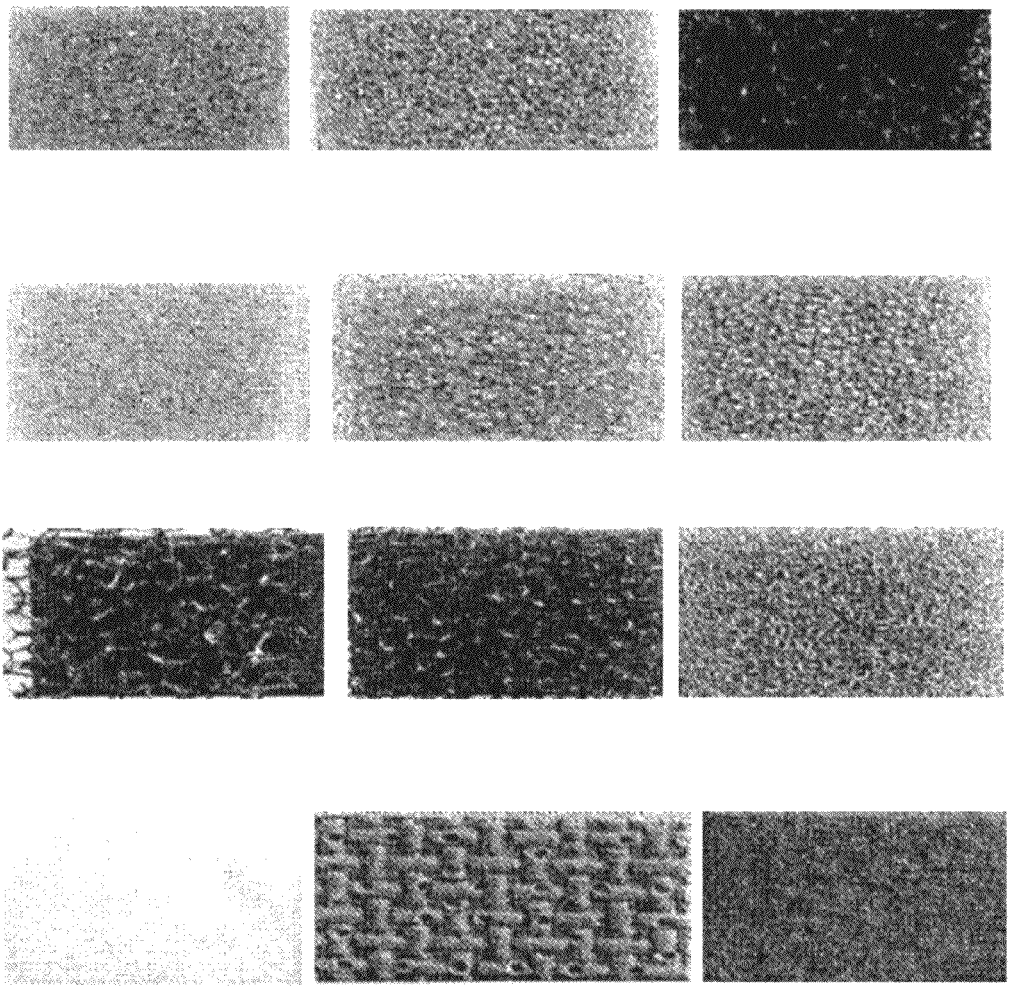
Figure 20:
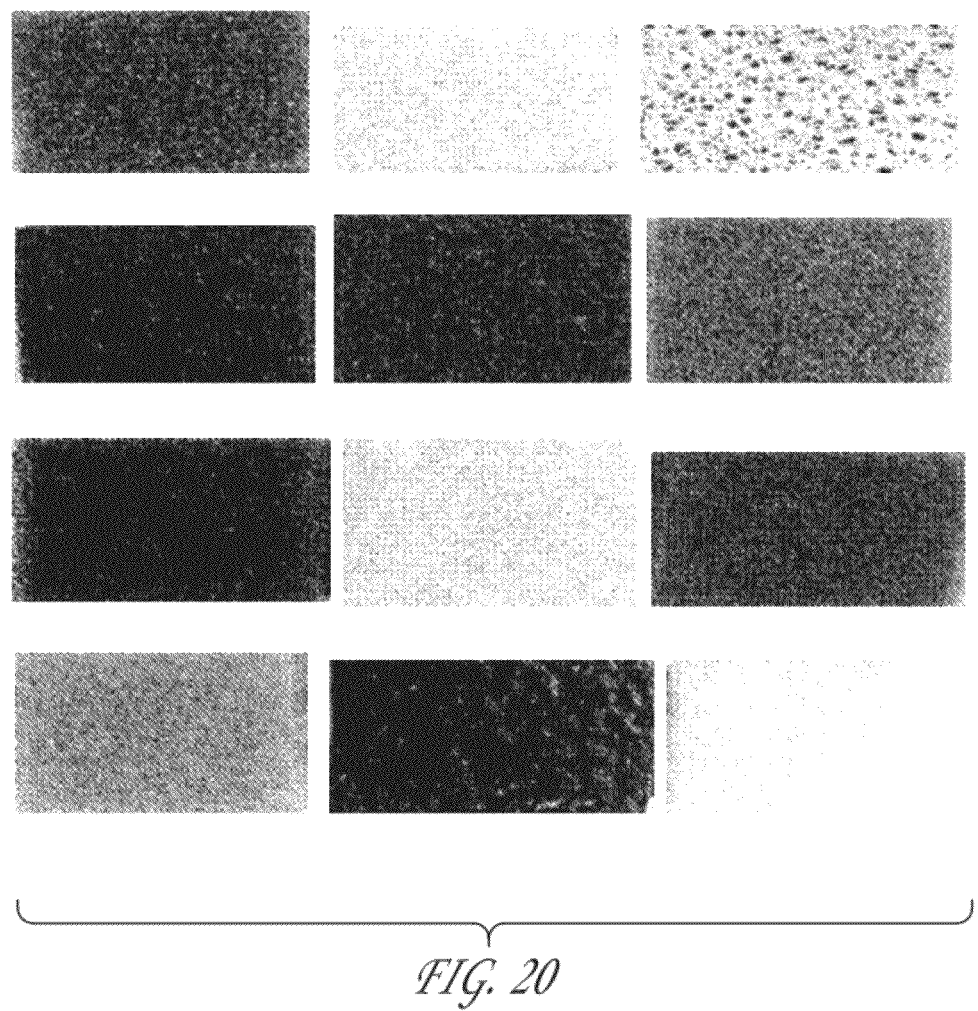
Figure 21:
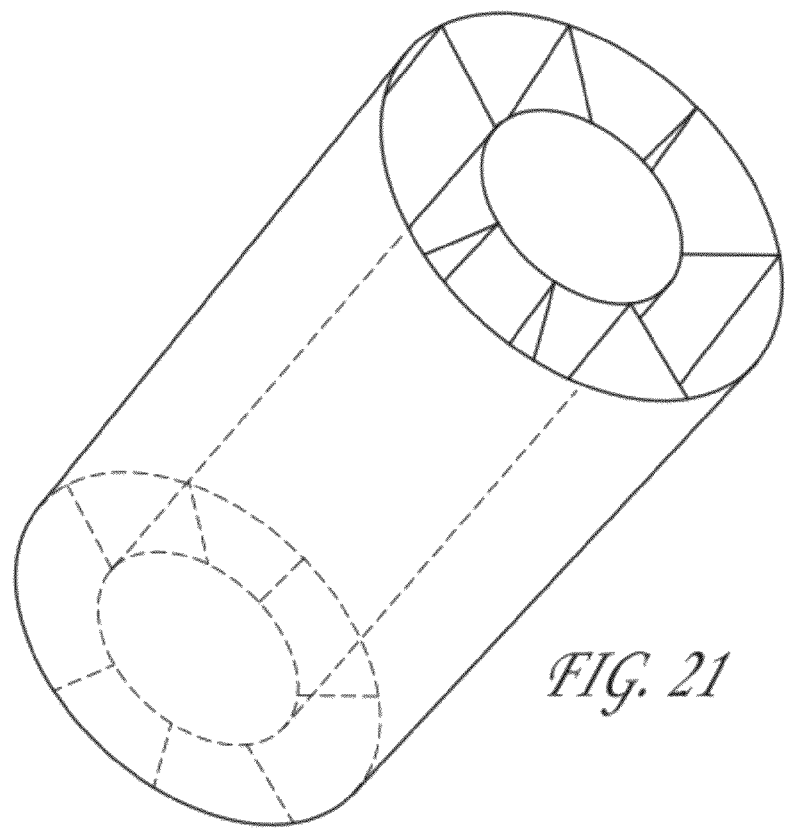
FIGS. 21 to 26 shows other exemplary designs for devices of the present invention.
Figure 22:
Figure 23:
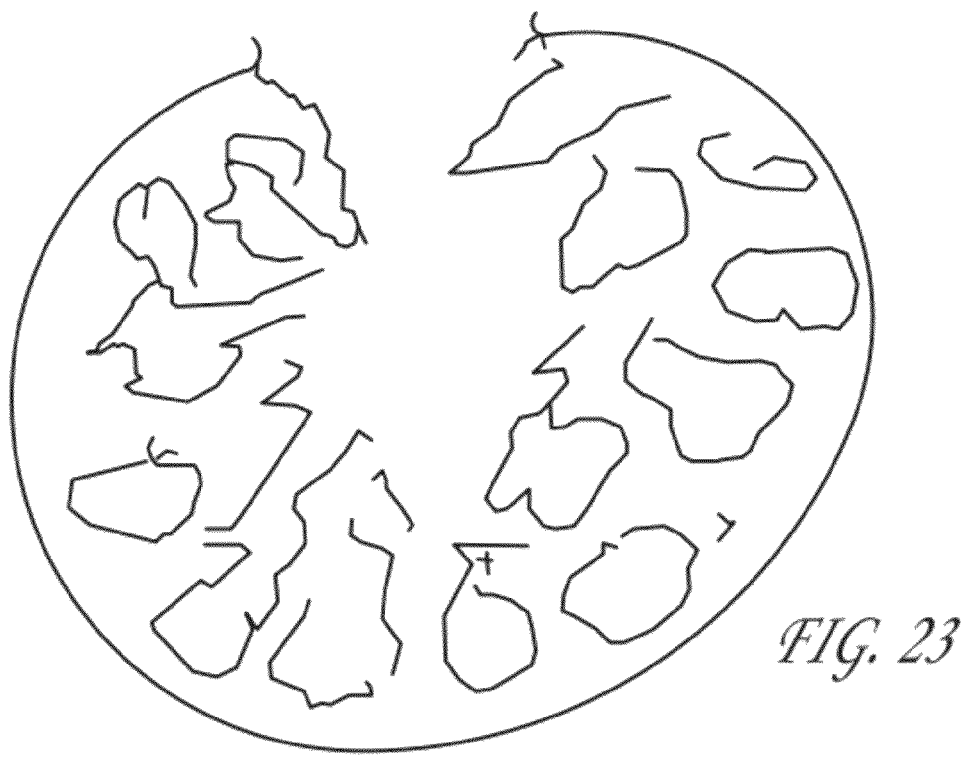
Figure 24:
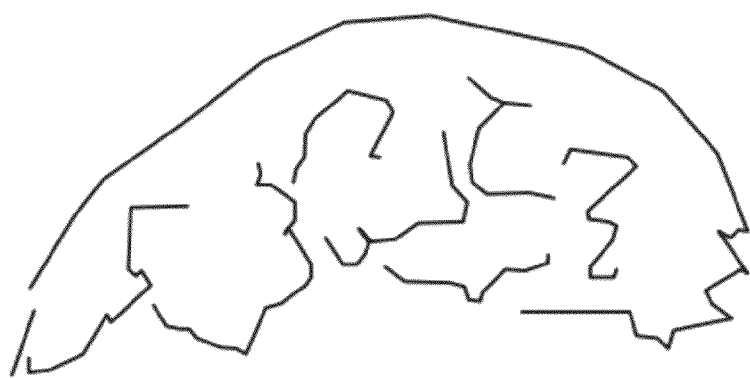
Figure 24:
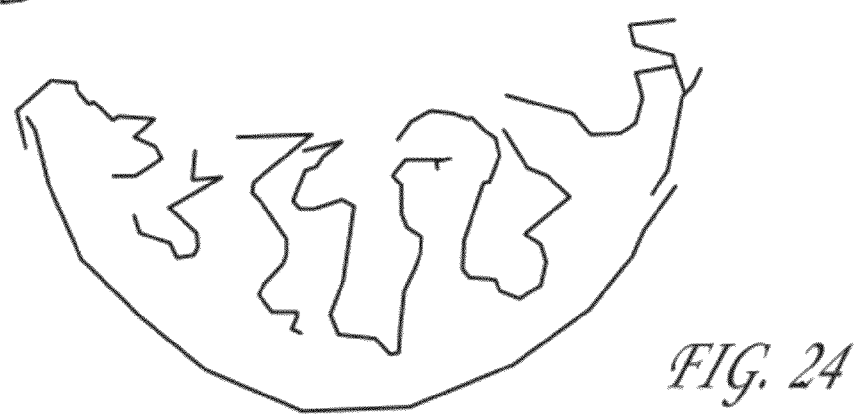
Figure 25:
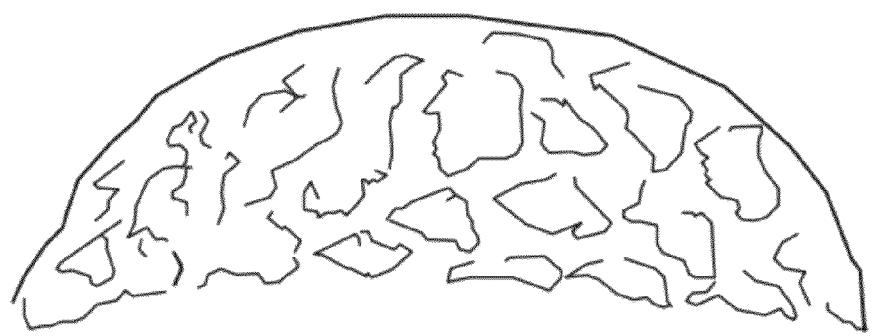
Figure 26:
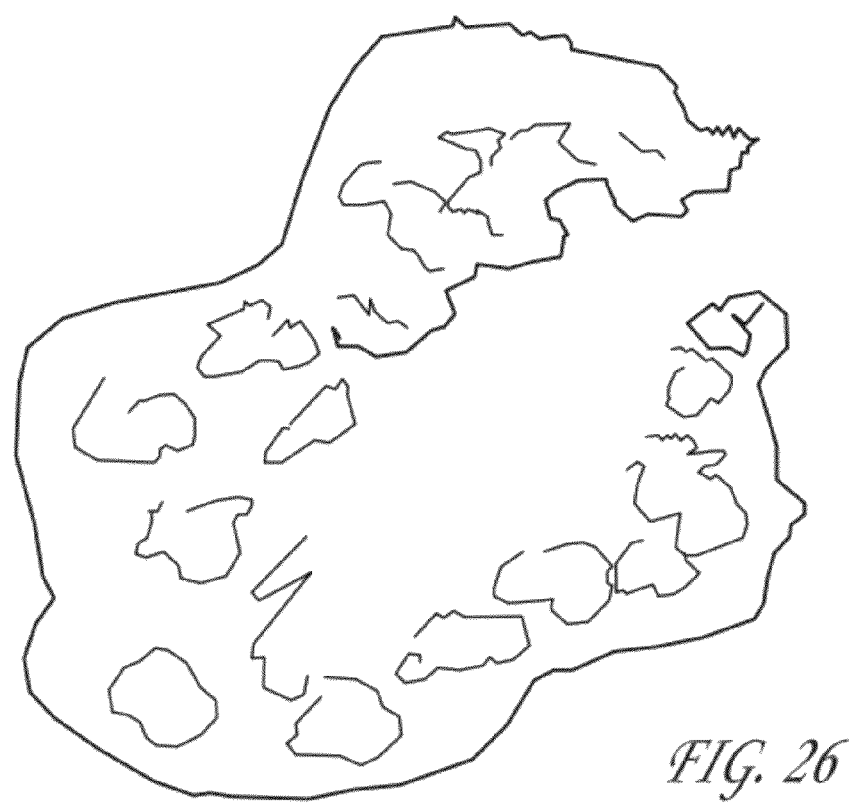

In some embodiments, the sponge material may be a conventional or natural sponge produced by conventional methods. In other embodiments, the sponge-type material may be produced from, e.g., foaming agents, reactive agents, percolating agents, and may be formed by extrusion, blow-molding, injection molding, thermoforming, mechanical or chemical carving and shaping, etc. Alternatively, the sponge material may be made by assembling of smaller segments and/or geometrical and/or random shaped units into larger units, allowing for careful selection of the sponge morphology. For example, the sponge material may be made by extrusions processes, blow-molding processes, injection or thermoforming molding processes., or may be mechanically and/or chemically printed or mechanically carved or formed. The sponge material may be partially or totally elastic, elastomeric, resilient or not, recoiling, or partially rigid or semi-rigid, and/or plastic. FIGS. 17-20 illustrate certain exemplary sponge materials which may be suitable for use in the present invention.

The sponge material is typically selected such that the cell walls will have "shape memory," namely, the cells generally at least partially return or expand to their original size and/or shape once an applied mechanical and/or chemically compression force is released.

The mechanism of expansion of the released sponge material may be, e.g., through the return of a shape memory material such that at physiological conditions in the stomach (e.g., at 37° C.) the material assumes at least partially its original shape. Elastomeric or resilient material may be employed for the sponge material, e.g., elastomeric, materials like latex, guayule, polyurethane rubber, silicon rubber, cellulose, nanocellulose, nitrile rubber, or biological materials such as elastin, collagen and/mother natural proteins, or any other suitable materials that can retain and conserve their original shape after extended periods of time under compression, or which return to the memory shape or assume a different shape. Alternatively, the mechanism of expansion may be largely clue to fluid absorption of the sponge, for example, when including such materials as hemicellulose, which has a high absorption strength, and is able to create a hydraulic force to inflate the sponge scaffolding.

The sponge matrix can be made of material safe for human ingestion. Examples of suitable materials include: polymer or copolymer of polyurethane, nylon, polyethylene, polypropylene, polyacrylate, EVA, natural rubber, silicon, silicon rubber, latex, epdm rubber, butile rubber, nitrile rubber, PVA, PLA. Suitable elastomeric biomaterials include silicones, thermoplastic elastomers, polyolefin and polydiene elastomers, polyvinyl chloride), natural rubber, guayule rubber, heparinized polymers, hydrogels, polypeptides, and elastomers, which may be compounded with other polymer or natural or artificial elastomers and or fillers like clay, starch, elastic fibers, elastic microfibers, elastic nanofibers, which may be further compounded with inert and/or natural compounds, such as cellulose and its derivates, elastic and non-elastic fillers and powders.

Other suitable materials for the matrix include natural polymers such as cellulose, nanocellulose, bacterial cellulose, cellulose fibers, microfibers and nanofibers, methylcellulose, ethylcellulose, ethylmethylcellulose, other cellulose derivatives, cellulose compounded with natural or synthetic or artificial elastomers and/or fillers and natural hydrogels like chitosan, opuntia, and other disaccharides, and natural clays (e.g., montmorillonite).

In certain embodiments, a sponge material may be employed which provides substantially all of the desired properties, e.g., swelling, absorbing soaking, shielding, retaining, disintegrating, and may further be biocompatible, biodegradable and may comprise only natural materials.

In embodiments where disintegration of the matrix material in the GI tract is appropriate or indicated, biodegradable fillers, compounds or fibers can be employed. The partial or total disintegration of these compounds, fillers or fibers in the digestive tract may induce the partial or total collapse of the sponge material. Accordingly, an average disintegration time of the material may be effected by adjusting the proportion of such additives. Exemplary fillers may include starches and/or other polysaccharides.

The size of the sponge matrix may range from, for example, a diameter of about 1 nm to about 25 mm, or about 1 µm to about 100 µm. The length of the present sponge tubes may range from, for example, about 1 µm to about 3". Accordingly, the geometry of the present "tubes" may vary according to the selected width and length. Furthermore, different sizes and shapes of sponges may be employed to selectively capture different particulate sizes and/or suspensions and/or colloids. Accordingly, a capsule may contain an assortment of sponges having various external geometries, sponge materials, sponge morphologies, etc.

Further, the sponge geometry may be selected to maximize packing or stacking efficiency, or maximize the number of sponges which may be compressed in a capsule, thereby maximizing the nutrient sequestrating capacity of each capsule.

The compositions and devices may further comprise other natural or synthetic materials to provide the desired mechanical properties, or desired absorptive and/or shielding properties.

In order to protect fluids absorbed by the present devices from being subsequently released, the fluids should be kept inside or sequestered in the matrix material once absorbed. Additionally, absorbed fluids or materials should be shielded from exposure to digestive enzymes. Accordingly, absorbed fluids may be gelled or made more viscous. Nutrients thus captured may be sealed or sequestered inside the tubes by one or more hydrogel(s), fiber(s) and/or gum(s). Such hydrogel(s), fiber(s) and/or gum(s) may be directly incorporated into the sponge material, compounded in the sponge walls matrix, contained and/or dispersed inside the sponge cells, or located at particular areas of the tubes, for example, the entrances or openings of the tubes as described herein.

Without being bound to any specific theory or explanation of the mode or mechanism of action, the present devices may act in part in a manner analogous to the behavior of dietary fiber (e.g., soluble and/or insoluble fiber) in the digestive system. That is, the compositions and devices may decrease and/or slow the absorption of nutrients, and/or may accelerate the passage of nutrients in the gastrointestinal tract. Thus, in certain embodiments, the compositions and devices may contain as much natural fiber as possible, either soluble, insoluble, or a combination of both. In certain embodiments, a combination of soluble and insoluble fibers are employed. Insoluble fibers may be included to provide, inter alia, desired mechanical properties as described herein including expanding and shielding. Insoluble fibers may also be included for their mucillagenic properties of gelling of fluids and/or increasing the viscosity of entrapped, bound, encapsulated or entrained fluids.

Non-limiting examples of suitable hydrogels include: polyvinyl alcohol, poly(ethyloxazoline), polyvinylacetate-polyvinylalcohol copolymers, poly(2-hydroxyethylacrylate), poly(2-hydroxyethylmethacrylate), carboxymethylcellulose, polyacrylic acid, and copolymers thereof, disaccharides, polysaccharides, chitosans, alginates, water soluble proteins, and polynucleic acids, natural clays (e.g., montmorillonite), sodium bentonite, absorbent fibers, super absorbent fibers, micro and nanofibers, micro and nanopowders, and combinations thereof.

Mixing of hydrogels and/or mucilage and/or gum forming compounds in the sponge material may result in the cells, pores or walls of the sponges becoming less permeable, and accordingly may inhibit entrance or exit of fluids after initial absorption or sequestration of digestive fluids. There are many different compounds that can achieve this effect, artificial and/or natural. Exemplary natural compounds may include soluble fibers, gums, etc. as described hereinabove. Individual hydrogels, gums or fiber material, or mixtures thereof may be selected to provide a desired absorption profile and/or other desired properties (e.g., expansion properties, absorption capacity, mechanical properties, etc.).

The hydrogel(s), fiber(s) and/or gum(s) dispersed in the sponge matrix or added thereto and contained mechanically in the tubes or tube cells may seal the cells, creating a multitude of sealed or partially sealed compartments where the movements of fluids may be partially or completely restricted in order to prevent leakage of absorbed nutrients or penetration by digestive enzymes as the sponge travels the GI tract prior to excretion. The hydrogel(s), fiber(s) and/or gum(s) in the sponge cell walls will swell up with fluids until the expansion of the sponge cells will seal totally or partially the axial holes. Another effect of the hydrogel(s), fiber(s) and/or gum(s) may be to make the sponge tube more mechanically stable or robust, in order to better resist the final passage in the colon in the event the tubes are to be naturally expelled by the body.

In some embodiments, nutrients are trapped in the sponge by the hydrogel(s), fiber(s) and/or gum(s), and the sponges then disintegrate after passage through the upper GI tract. For example, these components may disintegrate after the portions of the GI tract where most nutrient absorption occurs, such that mechanical stability may not be necessary. In this case, the sponge material can be selected such that the material at least partially or totally disintegrates in the lower GI tract, to assure safety in the case of excessive consumption of tubes or in a clinically slow discharging intestine (e.g., to avoid intestinal blockages).

In some embodiments, the compositions and devices comprise insoluble and soluble dietary fibers, such as resistant starches, non-resistant starches, and non-starch polysaccharides. Examples include arabinoxylans, cellulose, dextrins, inulin, lignin, waxes, chitins, pectins, beta-glucans and oligosaccharides, including galactosaccharides and fructo-oligosaccharides. Other exemplary polysaccharides include etheropolysaccharides like pectines. The compositions and devices may employ a mixture of different insoluble fibers, mixtures of different soluble fibers, and/or mixtures or one or more of each of insoluble and soluble fiber(s). In certain embodiments, a mixture of the two types of fibers (e.g., insoluble and soluble) may be employed. Insoluble fiber(s) may provide a "sponge" skeleton and/or may provide a shielding functionality.

In certain embodiments, the composition or device comprises one or more soluble fiber(s) selected from an exopolysaccharide mucilage. The exopolysaccharide mucilage may be from *Aloe vera, Basella alba* (Malabar spinach), Cactus, *Chondrus crispus* (Irish moss), *Dioscorea opposita* (Nagaimo, Japanese mountain yam), *Drosera* (sundews), fenugreek, flax seeds, kelp, liquorice root, marshmallow, mullein, okra, *Parthenium, Pinguicula* (butterwort), psyllium seed husks, *Salvia hispanica* (chia) seed, *Ulmus* rubra bark (slippery elm), or any other suitable plant.

In these and other embodiments, the compositions and devices may comprise cellulose or derivatives of cellulose like methyl cellulose, ethyl cellulose, and/or methyl-ethyl cellulose.

In these and other embodiments, the compositions and devices may comprise natural gums, such as those that may be obtained from seaweeds and other sources. Such compounds include polyelectrolytesagar (E406), alginic acid (E400) and sodium alginate (E401); and Carrageenan (E407). Natural gums obtained from non-marine botanical resources include polyelectrolytes: gum arabic (E414) from the sap of *Acacia* trees, gum ghatti from the sap of *Anogeissus* trees, gum tragacanth (E413) from the sap of *Astragalus* shrubs, and karaya gum (E416) from the sap of *Sterculia* trees. Other natural gums include guar gum (E412) from guar beans, locust bean gum (E410) from the seeds of the carob tree, beta-glucan, from oat or barley bran, chicle gum obtained from the chicle tree, dammar gum from the sap of Dipterocarpaceae trees, glucomannan (E425) from the konjac plant, mastic gum, a chewing gum obtained from the mastic tree. In certain embodiments, the mucilage material includes *Psyllium* seed husks from the *Plantago* plant, spruce gum from spruce trees, tara gum (E417) from the seeds of the tara tree, and/or natural gums produced by bacterial fermentation, e.g., polyelectrolytes: gellan gum (E418) and xanthan gum (E415). Fibers of animal origin, such as keratins (e.g., silk, etc.), elastin and/or collagen may also be employed. These natural gums or fibers may be obtained from commercial sources.

The hydrogel(s), fiber(s), waxes, and/or gum(s) may provide an additional mechanism (or force) for expansion of the matrix material, by providing a chemical expansion, e.g., via absorption of water and other fluids. For example, the matrix material may expand, or hydrogel(s), fiber(s) and/or gum(s) which may be present in the sponge cell walls may absorb water and fluids and stiffen the cell walls to return the sponge tube at least in part to its original size and/or shape prior to compression and/or stacking.

In some embodiments, the device or composition comprises hemicellulose or xylan, alone or compounded chemically and mechanically. This short chain polysaccharide (hemicellulose) is inexpensive and has a great capacity to absorb fluids. For example, the device or composition may comprise hemicellulose-citrate-chitosan, in an aerogel foam, which is both elastic and extremely absorbent. In these or other embodiments, the device or composition comprises, or further comprises one or more fillers such as crystalline cellulose and/or amorphous cellulose, lignin or other stiffening compounds. In such embodiments, an expansion mechanism of the matrix is in part a result of absorption of fluids, which may stiffen the scaffolding material of the sponge, and may magnify the total expansion.

In some embodiments, the composition or device comprises an ester of hemicellulose with organic acid (e.g., having carboxylic groups). Examples include hemicellulose citrate, hemicellulose acetate, and other organic acids, which make a foam having desirable flexibility and elastic recoil. In other embodiments, the composition or device comprises hemicellulose alone or with chitosan. Still further, embodiments of the device or composition may employ starch-citrate-chitosan, starch-chitosan, or starch-hemicellulose-chitosan.

In order to obtain the desired gelling action, additional compounds may be included, in the presence or absence of hemicellulose-citrate-chitosan. Such compounds include various types of cellulose or other artificial and synthetic compounds, such as one or more of: bovine serum albuminate pectinate, pectine-ethyl cellulose, calcium pectinate and chitosan, naproxen pectin, de-esterified pectin, zinc-pectinate gels, amylose, chondroitin-sulfate (crosslinked or uncrosslinked), cyclodextrins, dextran, calcium alginates and alginates, locust bean gum, guar gum, glutaraldehydes, and epiclorihydrine. For example, in certain embodiments, guar gum is employed, which may be compounded or just dispersed in the hemicellulose matrix foam sponge.

Another mechanism for expansion of the matrix material may include incorporation of a combination of compounds and/or protein-like substances or structures, arranged in a fashion analogous to muscle structure, wherein the shrinking, expanding and/or twisting of one component with respect to another may cause a rolling and/or twisting or expanding action, resulting in the expansion of the material.

Still another mechanism for releasing the compressed matrix material may include foaming and/or gas releasing agents activated by the heat and/or acid environment of the stomach, which may produce gases and/or foaming to expand the material (e.g., $NaHCO_3$, etc.). As such, in the case of a sponge material reacting to the acidic environment of the stomach, all or part of the material of the sponge may react with the stomach acid, increasing at least partially in volume, and returning the sponge to its original shape. The matrix material, which is typically released into the stomach after dissolution of a capsule (e.g., a gelatin capsule or the like) containing the compressed material, typically expands inside the stomach and absorbs the fluids therein.

Yet another mechanism of expansion may include electrostatic and/or magnetic repulsion and/or attraction of some parts of the sponge with other parts of the sponge, or the electrostatic interactions or a tube with another tube or similar entity included in the pill or introduced into the stomach independently. In still other embodiments, the matrix material might be introduced as twisted shapes with an elastic expansion mechanism as described above, which can then untwist and expand.

In certain embodiments, the capture of nutrients may also be caused by the twisting (e.g., like the wrapping of a caramel) or rolling of the matrix material. In such cases, the matrix material may have a flat geometric configuration, although such a mechanism may be possible with other shapes and may also comprise an absorbing mechanism associated with the sponge material. Such twisting and/or rolling may be caused or induced by one or a combination of the above mentioned mechanisms.

Figure 2:
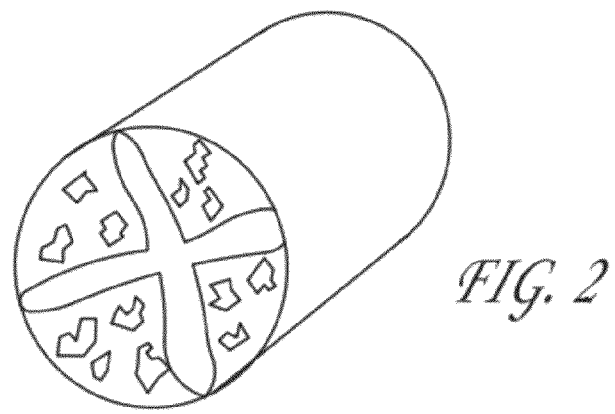
Figure 3:
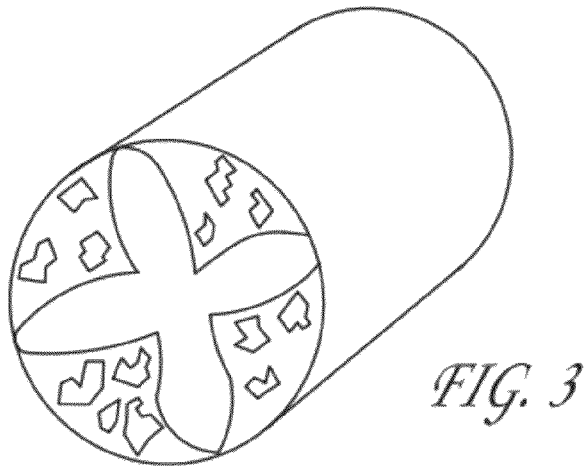
Figure 4:
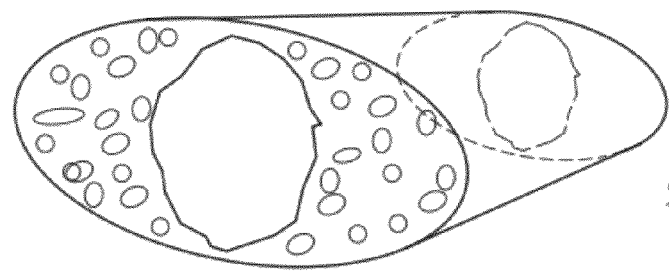
Figure 5:
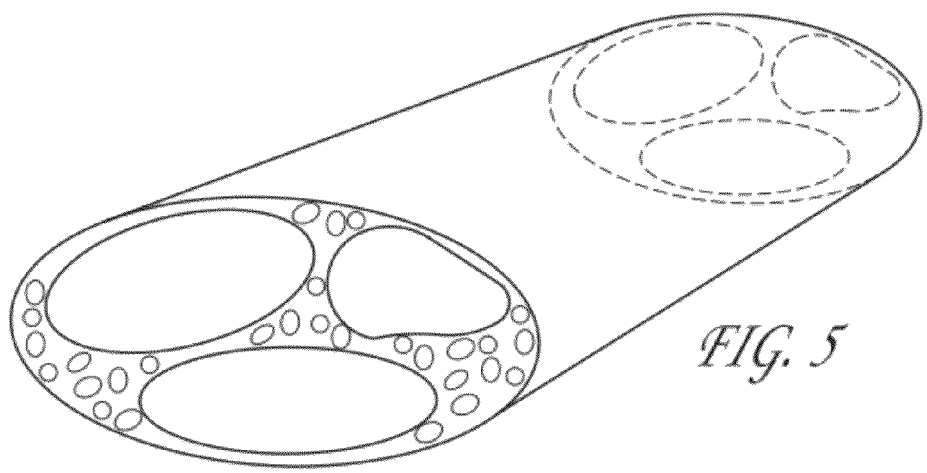
Figure 6:
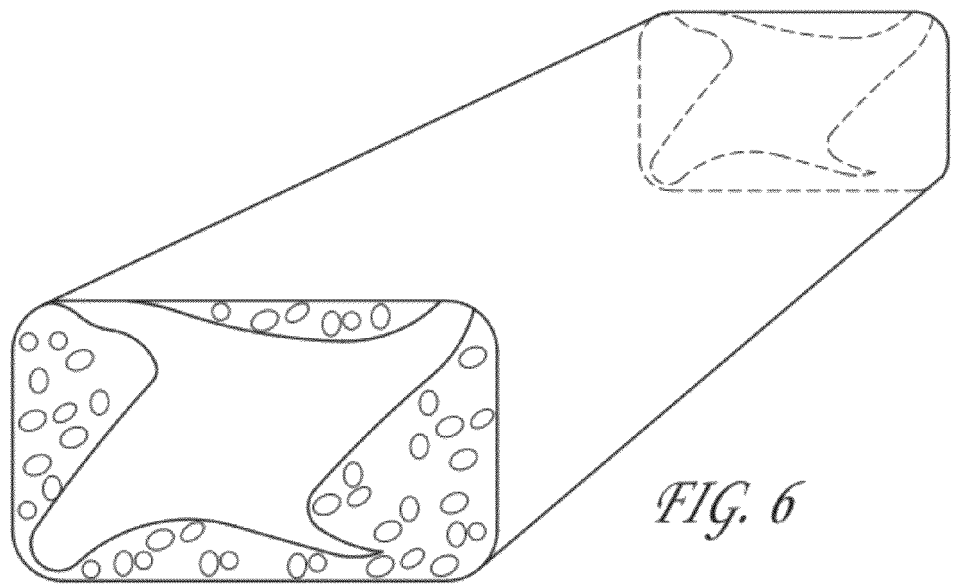
Figure 7:
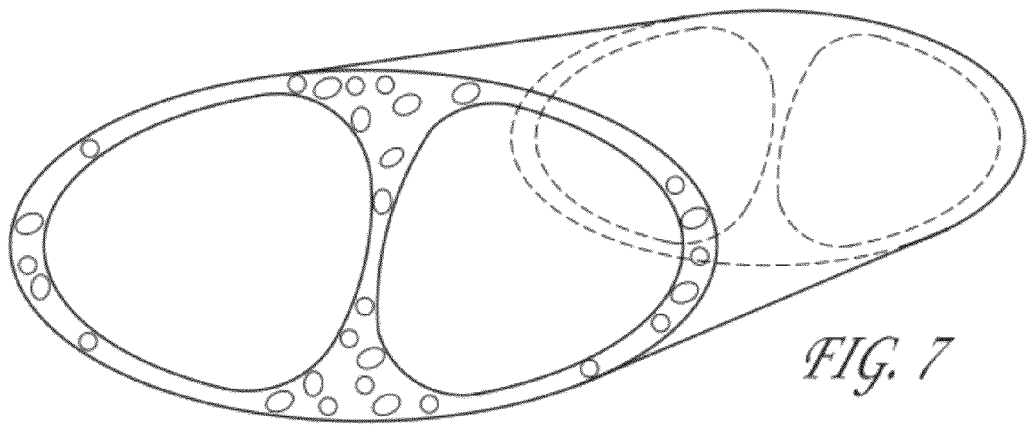
Figure 8:
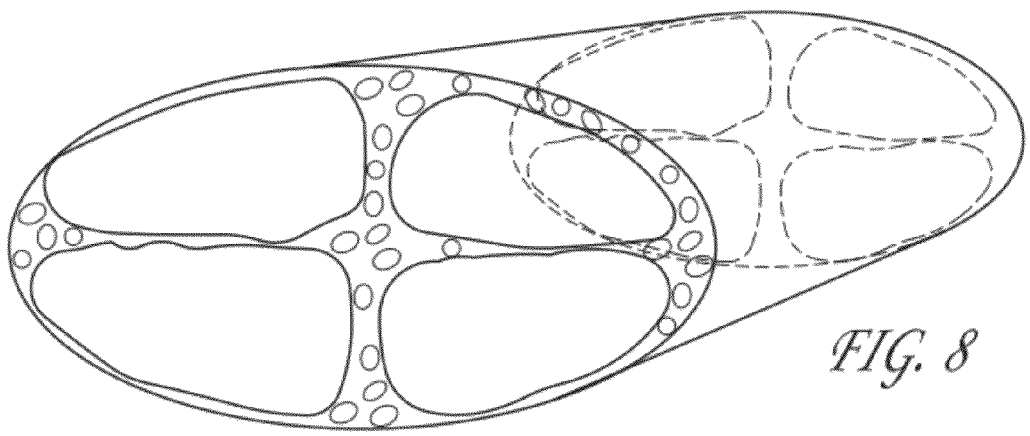
Figure 9:
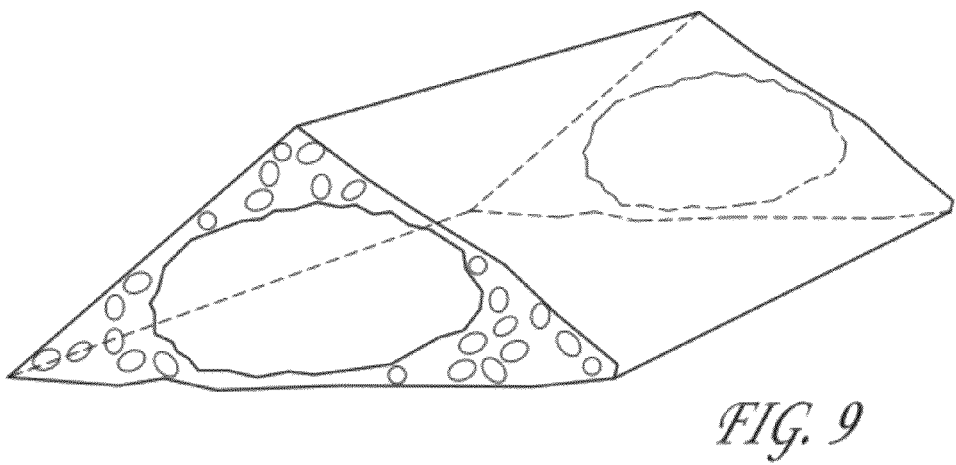
Figure 10:
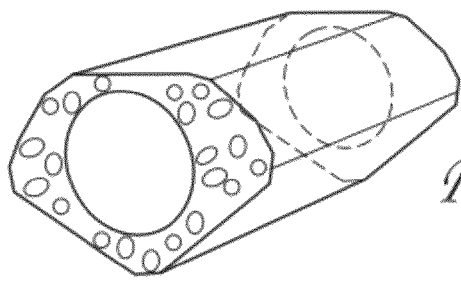
Figure 11:
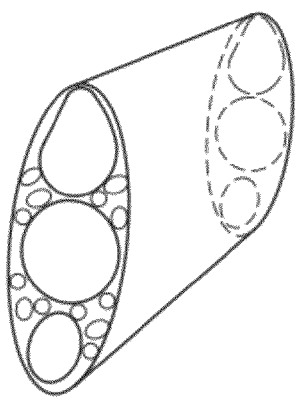
Figure 12:
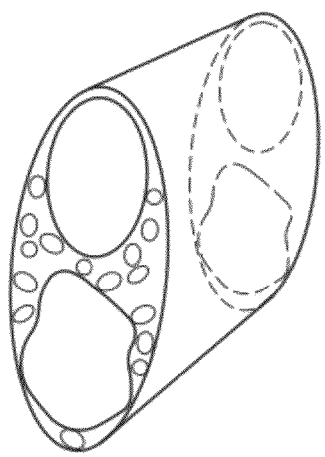
Figure 13:
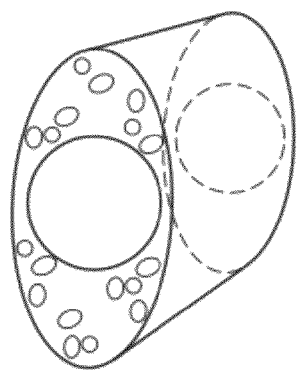
Figure 14:
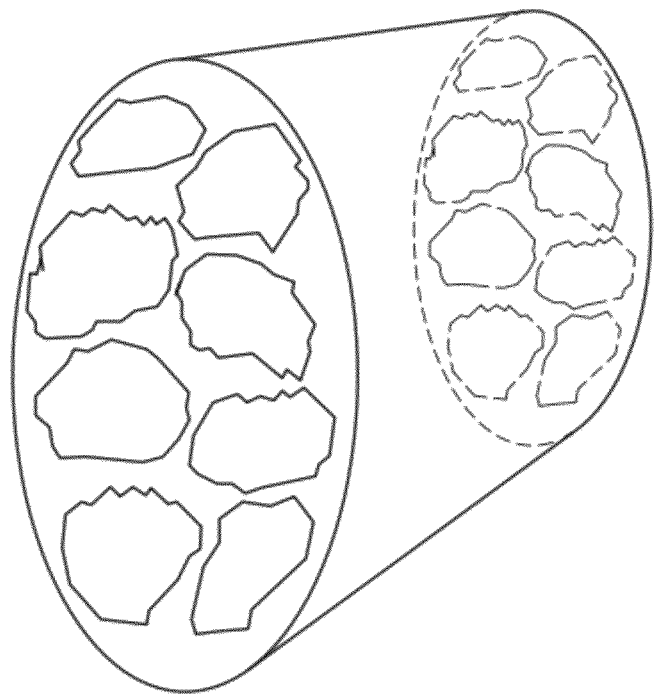
Figure 15:
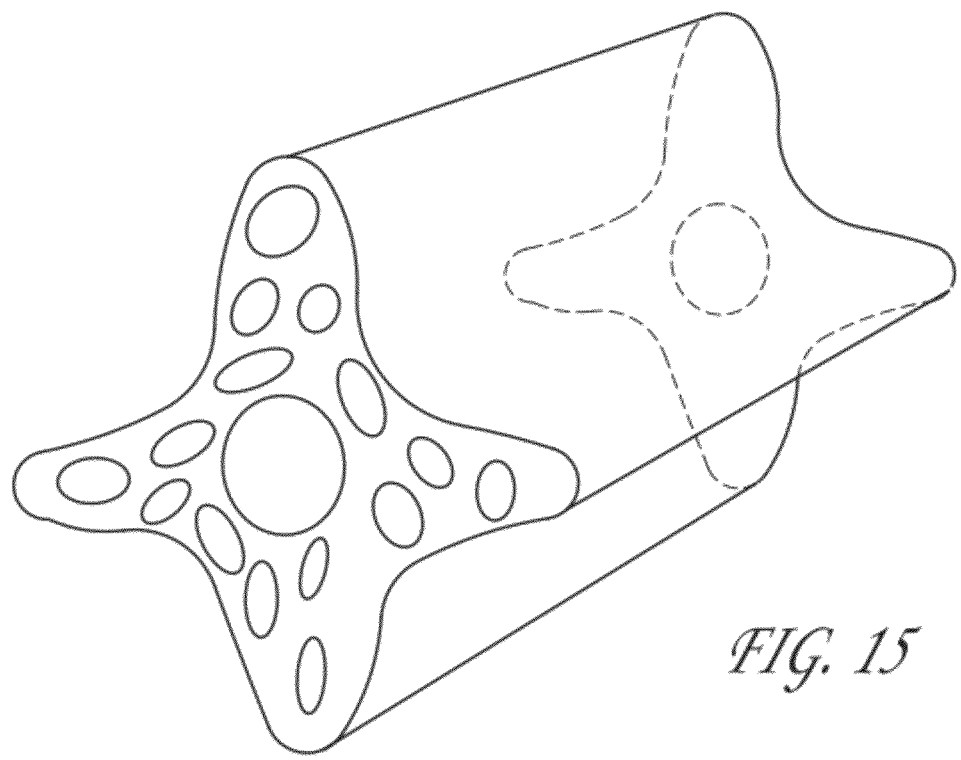
Figure 16:
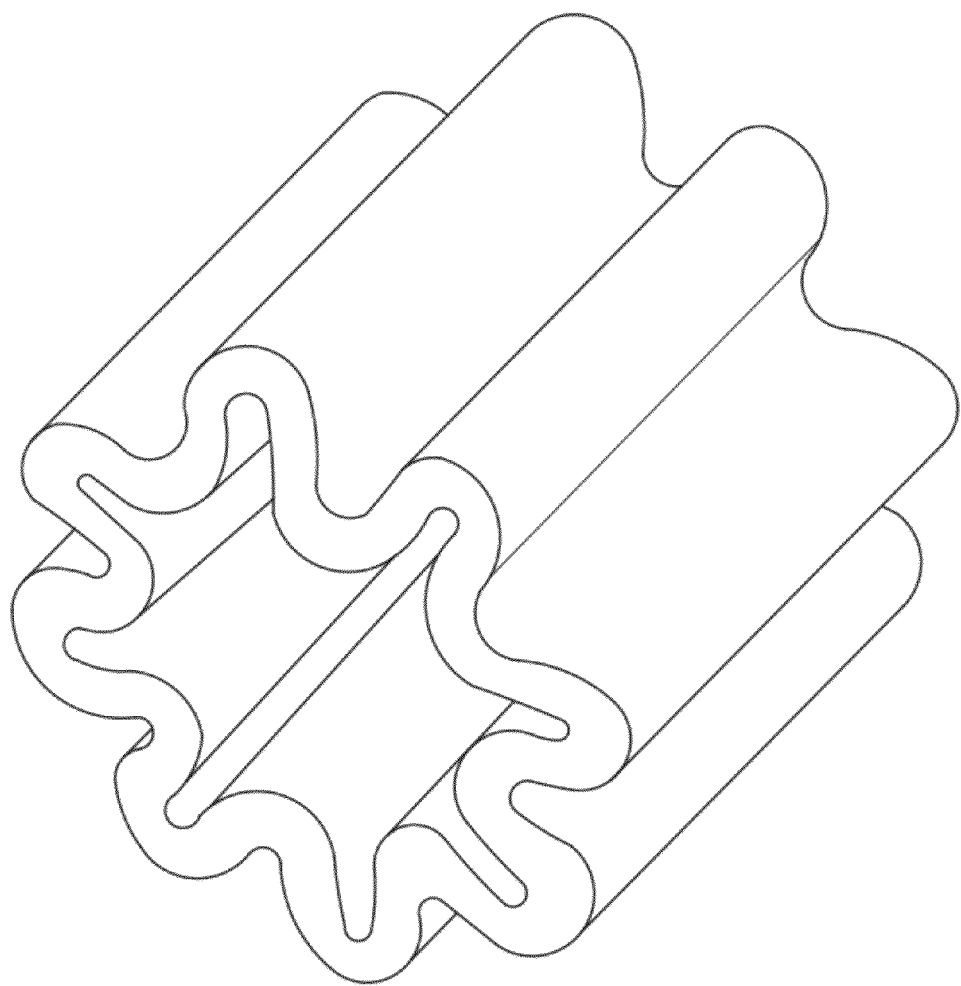

The matrix material may be cylindrical, and may have an elliptical, oval, square, rectangular, triangular or polygonal or trapezoidal cross-section or shape. Further, various regular or irregular shapes or cross sections may be used in forming the compositions and devices, and a given "tube" may comprise one or more discrete domains of a particular shape or cross-section. The geometries and cross sections may support efficient packing, e.g., into capsules, such that a sufficient amount of "tubes" may be delivered in a small space. The geometries, cross sections, and opening configurations may further allow efficient absorption of stomach digestion products. Mixed geometries or shapes are also possible. FIGS. 1-16 illustrate a number of exemplary shapes and cross-sectional geometries. Further, as illustrated, the matrix material will typically have one or more axial openings or holes along its longest axis, although more than one hole may exist along essentially any axis. FIGS. 1-16 illustrate a number of possible hole configurations.

The hole(s) may be centered along the main axis (e.g., along the longest side) of the tube, or may be off center. The hole(s) can have a circular, star, cross or other segmented geometry (see FIGS. 1-16). The purpose of this hole is to facilitate rapid absorption of nutrients in the stomach. The sponge architecture with holes is designed to facilitate the entrance and capture inside the sponge of larger sized particulates that otherwise might be absorbed in the interior of the sponge. Furthermore, the hole(s) generally decrease the volume of the compressed tube inside the capsule, so more tubes can be accommodate in a single capsule and a larger volume of nutrients can be sequestered or with a single pill.

In some embodiments, the device or composition may comprise one or more releasing agents in the cavity or in the cavities, or in cells of the sponge, in order to avoid sticking between the walls of the cell. Such releasing agents could be natural or artificial waxes, wax compounds with a gum for elasticity, or just a small layer of a polymer such as polyethylene compounds or polyethylene glycols or just polyethylene. In certain embodiments, the releasing agent dissolves in the stomach or is a natural foaming agent (e.g., baking soda).

The external skin of the matrix material can be essentially intact, smooth and free of perforations or holes, or may have some holes, which may be small in some embodiments. Such totally or partially intact skin may avoid loss of absorbed nutrients from the matrix material due to mechanical and enzymatic action of the digestion. However, in some embodiments, the exterior of the matrix material is essentially the same as the interior, and may be perforated or the like.

Nutrients to be absorbed generally enter the matrix material via the openings, which may be present at the ends where no skin is present, or at the open ends of holes through the tubes. The sponge geometry and the number and placement of tubes in the sponge can be selected to accommodate the greatest possible number of tubes inside a fixed capsule volume, to assure the best possible shape memory return once the tubes are released from the capsule, to maximize absorption of each tube, or a combination of these or other factors.

The matrix material may be manufactured by normal extrusion, or by foaming of a block of material, after the mechanical cutting of the desired shape. Alternatively, the matrix material could be punched from a fast advancing strip. The matrix material may be encapsulated by nip rolling a sheet of the sponge material. The rolls may be running films of a packing or protecting compounds, as used often in the pharmaceutical industry. For example, the material may be PLA or other natural or artificial material. The nip rolls compress and cut the matrix material at the same time, and in other rolls print and seal the films around the sponge. A plurality of these printed sponges contained by the double films are deposited in a normal gel cap capsule or other similar container. A similar process, although more miniaturized, could be employed to make sponges for premixing with food products. The "sponge" matrix, scaffolding, could alternatively be manufactured by mechanically punching holes in the main scaffolding material (e.g., foam), and after folding the holed, cored, celled material on itself, rolling or folding, and gluing or mechanically fastening the holed strip in order to retain a three dimensional structure, and then compressing and encapsulating it. The rolls could further be designed, not just to flatten the sponges, but to give a lateral compression as well.

Depending on the size, the invention may employ encapsulation, microencapsulation, or nanoencapsulation of the matrix material. Such encapsulation techniques as known, for example, and are used for micronutrients or drug delivery. In some embodiments, the devices and compositions are encapsulated with casein. Techniques for micro or nanoencapsulation include: pan coating, air suspension coating, spray-drying, ionotropic gelation, coacervation, in situ polymerization. In other embodiments, the sponges are encapsulated by freezing in a compressed state. With a small amount of water, once compressed and frozen, the sponge matrix will stay compressed allowing easy encapsulation.

For weight loss or weight control, the composition or device as described is ingested before, during or after meals or any other food ingestion, e.g., breakfast, a snack, etc. The capsules can be specially tailored for large or small size human bodies and/or for light or heavy meals by adjusting the capsule size, and accordingly, the number of tubes and the total absorptive capacity of the capsule. Once a capsule comprising. For example, the "sponge tubes" is ingested and in the stomach or the intestine, the capsule dissolves, releasing the tubes either all at once, or in groups (e.g., in delayed release). The released tubes, no longer mechanically or chemically constrained by the capsule, will then expand, absorbing, capturing, enclosing, soaking some fraction of the contents of the stomach or intestine present at the moment of the tubes are released.

In some embodiments, the composition or device may be used directly in food products (e.g., mixed therewith) to reduce the caloric content of the food containing the devices. For example, the present devices may be dispersed, added, and/or mixed in a food product, or included as a separate component in a packaged food product for addition to the food product (e.g., in prepackaged food products, with food served at a restaurant, or with food at home, in beverages, etc.). In one embodiment, the present devices) (e.g., capsules, etc.) may be scaled or sized such that they may be mixed with or added to prepared foods. For example, small sponge "drops" having, e.g., spheroidal or ellipsoid geometry, with dimensions of, for example, less than about 500 µm, less than about 250 µm, less than about 100 µm, less than about 50 µm, less than about 40 µm, less than about 30 µm, less than about 20 µm, less than about 10 µm, less than about 5 µm, or less than about 1 µm (or any other value or range or values therein or therebelow) could be on or in, e.g., chocolate, spreads, jams, peanut butter, butter, cereals, flours, sweets, candies, cakes, dough, pastas, sugars like sucrose or fructose or high fructose corn syrup, even soft or alcoholic drinks, juices and/or any other food generally for sale or served in restaurants.

The small size of these capsules may allow them to avoid being destroyed during mastication, and may render them undetectable by the taste buds. For example, the compositions may be tasteless, and/or may be scaled such that they provide a smooth "mouthfeel". Once in the stomach, the devices or "drops" would be released from any encapsulating material and could then expand, absorb fluids, and, in embodiments wherein the devices are designed to do so (e.g., as described herein), gel the absorbed or encapsulated fluids.

In the case where foods which contain the present devices require further cooking and/or preparation (e.g., flours, pasta, etc.), an encapsulation material may be selected to resist exposure to heat and/or exposure to cooking fluids. Such encapsulation may be effected by materials that may resist such thermal and/or fluid exposure, but may otherwise degrade or dissolve in the GI tract. For example, an encapsulation material may be selected that is heat resistant and/or heat stable, and fluid resistant at normal pH, but dissolves in an acidic environment (e.g., such as that in the stomach). Exemplary materials include polylactic acid (PLA), which may be resistant to temperatures as high as 190 degrees centigrade.

The device and compositions may be used to absorb and prevent digestion or biological effects of toxins or alcohol that is willingly or unwillingly ingested. In these embodiments, the device or composition need not be used routinely, but may be taken with food that is at risk of containing toxin, or upon knowledge of toxin ingestion, or may be used to avoid or counter the effects of alcohol overconsumption.

The following non-limiting examples will illustrate various aspects of the present invention. The examples should, of course, be understood to be merely illustrative of only certain embodiments of the invention and not to constitute limitations upon the scope of the invention which is defined by the claims that are appended at the end of this description.

EXAMPLES

In one example, a commercially available pure cellulose sponge was obtained. The sponge was cut into small tube-like shapes having a diameter of approximately 3-4 mm and a length of approximately one inch. The strips were then coated in carboxymethylcellulose (CMC) powder (a hydrogel). The cut, hydrogel coated strips were then inserted into polyethylene terephthalate (PET) tubes having approximately 6 μm thick walls (e.g., $1/10^{th}$ the thickness of a hair) and an internal diameter of about 4-5 mm. A batch of approximately 100 of these PET tubes filled with sponges was prepared.

Bundles of 20 of these sponge-filled PET tubes were then aligned longitudinally, compressed, and inserted in gelatin capsules approximately 25 mm long and approximately 9 mm in diameter to form "pills." Each pill weighed approximately 500 mg.

Commercially available canned chicken soup was obtained and poured into a plastic container. Sugar, salt, and lemon juice were added to the chicken soup to simulate the conditions (e.g., acidity) and contents of the stomach after food has been ingested. The mixture was then warmed to a temperature of about around 35-40° C.

One pill, prepared as described above, was then placed in the mixture, and the mixture was stirred for several minutes. After approximately 2.5 minutes, the gelatin capsule dissolved and began releasing the sponges. The sponges released from the dissolving gelatin capsule began to swell. Stirring was continued for approximately 10 minutes.

The soup-saturated sponges were then removed from the mixture with a strainer and weighed. This experiment was repeated another 4 times, for a total of five experiments. The total weight of the sponges ranged from about 13 grams to about 19 grams.

The sponge tubes were more rigid after absorbing the soup mixture. The fluid mixture had entered the sponge cells, wherein those fluids were gelled by CMC. Thus, in an exemplary experiment, from an initial weight of 0.5 grams to a final weight of 19 grams, the sponges had absorbed approximately 18.5 grams of the soup mixture.

Based on a an estimated caloric content of the soup mixture of about 4 kcal/g, and taking in consideration the dilution of the soup with water, it was calculated that an exemplary pill could absorb approximately 72 kcal of nutrients, which would be sequestered from absorption and metabolism in the GI tract. Thus, for example, 5 pills as described would be able to sequester nutrients equivalent to a small hamburger from the daily diet of a user. Accordingly, a person consuming approximately 5 of the exemplary pills with food could lose approximately 15 pounds of body weight per year.

Further development and refinement of the present sponge materials, geometries thereof, hydrogels employed, and packaging of the sponges as described herein will significantly improve the caloric absorption capacity of the present sponges and pills containing the same. For example, a sponge pill having an approximate volume of 2.5 cm$^3$, containing sponges prepared from a sponge material that expands and absorbs approximately 100 times its original volume, could capture up to approximately 250 cm$^3$ of fluid. That volume (i.e., 250 cm$^3$) equates to at least 250 grams of nutrients, and therefore may achieve a caloric sequestration of approximately 1,000 kcal per pill.

The embodiments described herein and illustrated by the foregoing examples should be understood to be illustrative of the present invention, and should not be construed as limiting. On the contrary, the present disclosure embraces alternatives and equivalents thereof, as embodied by the appended claims.

What is claimed is:

1. A device that absorbs and retains digested material in the stomach, the device comprising:
   one or more members of a compressible absorbent matrix material having a size, shape and/or geometry that is packed into a compressed delivery vehicle that is less than 50% of an expanded size of the delivery vehicle, wherein the absorbent matrix material forms a sponge architecture, including a plurality of cells defined by cell walls; and
   one or more sealing compounds contained in the cell walls.

2. The device of claim 1, wherein said absorbent matrix material has a defined shape.

3. The device of claim 1, wherein said absorbent matrix material is a tube.

4. The device of claim 3, wherein the tube comprises one or more interior voids in communication with an exterior.

5. The device of claim 4, wherein said one or more interior voids have defined shapes.

6. The device of claim 1, wherein said absorbent matrix material comprises an elastomer, latex, guayule, polyurethane rubber, silicon rubber, cellulose, nanocellulose, nitrile rubber, elastin, collagen or combinations thereof.

7. The device of claim 1, wherein the device regains its original shape after being compressed.

8. The device of claim 1, wherein the one or more sealing compounds are selected from hydrogels, soluble or insoluble fibers, waxes and gums, or mixtures thereof.

9. The device of claim 8, wherein said hydrogels comprise polyvinyl alcohol, poly(ethyloxazoline), polyvinylacetate-polyvinylalcohol copolymers, poly(2-hydroxyethyl-acrylate), poly(2-hydroxyethylmethacrylate), carboxymethylcellulose, polyacrylic acid, polyacrylic acid copolymers, disaccharides, polysaccharides, chitosan, alginate, water soluble proteins, polynucleic acids, natural clays, montmorillonite, sodium bentonite, absorbent fibers, super absorbent fibers, microfibers, nanofibers, micropowders, nanopowders, or combinations thereof.

10. The device of claim 8, wherein the device comprises an exopolysaccharide mucilage, cellulose, cellulose derivatives, hemicellulose, keratin, elastin, collagen, or mixtures thereof.

11. The device of claim 8, wherein the device comprises agar, alginic acid, sodium alginate, carrageenan, gum Arabic, gum ghatti, gum tragacanth (E413), karaya gum, guar gum, locust bean gum, beta-glucan, chicle gum, dammar gum, glucomannan, mastic gum, psyllium seed husks, spruce gum, tara gum, gellan gum, xanthan gum, or mixtures thereof.

12. The device of claim 1, wherein the absorbent matrix material has a flat geometric configuration.

13. The device of claim 1, wherein the device is in the form of a capsule.

14. The device of claim 1, wherein the device traverses the gastrointestinal tract of a subject and remains intact, without perforations or holes.

15. The device of claim 1, wherein said device dissolves in the gastrointestinal tract of a subject.

16. A method for sequestering nutrients or compounds from absorption in the digestive tract, comprising ingesting the device of claim 1.

17. A method for treating obesity, comprising providing the device of claim 1, to an obese subject.

18. The method of claim 16, wherein the device is used routinely.

19. A food product or beverage, comprising the device of claim 1.

20. A kit comprising a food product or beverage and a device of claim 1.

* * * * *